(12) United States Patent
Douglas

(10) Patent No.: US 6,629,949 B1
(45) Date of Patent: Oct. 7, 2003

(54) MICRO INFUSION DRUG DELIVERY DEVICE

(75) Inventor: Joel S. Douglas, Los Altos Hills, CA (US)

(73) Assignee: Sterling Medivations, Inc., Norcross, GA (US)

(*) Notice: Subject to any disclaimer, the term of this patent is extended or adjusted under 35 U.S.C. 154(b) by 0 days.

(21) Appl. No.: 09/672,456

(22) Filed: Sep. 29, 2000

Related U.S. Application Data

(60) Provisional application No. 60/202,818, filed on May 8, 2000, and provisional application No. 60/223,630, filed on Aug. 8, 2000.

(51) Int. Cl.[7] ................. A61M 37/00; A61B 17/34
(52) U.S. Cl. ................. 604/46; 604/19; 606/186
(58) Field of Search .................. 604/19, 20, 46, 604/47, 117; 600/556; 606/186, 183

(56) References Cited

U.S. PATENT DOCUMENTS

| | | | |
|---|---|---|---|
| 3,595,231 A | * | 7/1971 | Pistor |
| 3,814,097 A | * | 6/1974 | Ganderton et al. |
| 3,963,380 A | | 6/1976 | Thomas, Jr. et al. |
| 3,964,482 A | | 6/1976 | Gerstel et al. |
| 3,964,484 A | | 6/1976 | Reynolds et al. |
| 4,235,234 A | | 11/1980 | Whitney et al. |

(List continued on next page.)

FOREIGN PATENT DOCUMENTS

| | | |
|---|---|---|
| EP | 0 295 075 | 12/1988 |
| EP | 0 323 321 | 7/1989 |
| EP | 0 561 122 A1 | 9/1993 |
| EP | 0 916 353 A1 | 5/1999 |
| EP | 0 937 475 A2 | 8/1999 |
| FR | 2 628 636 | 9/1989 |
| WO | WO 93/17754 | 9/1993 |
| WO | WO 95/09021 | 4/1995 |
| WO | WO 97/36623 | 10/1997 |
| WO | 99/47341 | 9/1999 |
| WO | 99/64580 | 12/1999 |
| WO | WO 99/64580 | 12/1999 |
| WO | 00/16833 | 3/2000 |
| WO | 00/35530 | 6/2000 |

OTHER PUBLICATIONS

Albisser, A.M., et al., "A Portable Precision Pumping System for Chronic, Programmed Insulin Infusion", Medical Progress Through Technology, 1978, vol. 5, pp. 187–193.

Tamborlane, W., et al., "Reduction to Normal of Plasma Glucose in Juvenile Diabetes by Subcutaneous Administration of Insuling with a Portable Infusion Pump", The New England Journal of Medicine, 1979, vol. 300, pp. 573–578.

Irsigler, et al., "Long–Term Continuous Intravenous Insulin Therapy with a Portable Insulin Dosage–regulating Apparatus", Diabetes, 1979, vol. 28, pp. 196–203.

co–pending application Ser. No. 60/202,818, filed May 8, 2000, inventor: Joel Douglas.

co–pending application Ser. No. 60/223,630, filed Aug. 8, 2000, inventor: Joel Douglas.

Primary Examiner—Chen Wen Jiang
(74) Attorney, Agent, or Firm—Burns, Doane, Swecker & Mathis, L.L.P.

(57) ABSTRACT

An infusion pump for use with standard pre-filled medication container and a drug delivery device for percutaneously administering a drug. The delivery device having a plurality of projections and a drug reservoir. The projections extend from the reservoir and are adapted for penetrating the stratum comeun for percutaneously administering a drug from the reservoir to produce a local or systemic physiological or pharmacological effect. The plurality of projections is formed by micro machining. The pump is made by using a micro-actuator and includes a housing having a lid which opens and closes so that the medication container can be inserted and supported in a delivery mode position.

8 Claims, 10 Drawing Sheets

U.S. PATENT DOCUMENTS

| | | | |
|---|---|---|---|
| 4,313,439 A | | 2/1982 | Babb et al. |
| 4,493,704 A | | 1/1985 | Beard et al. |
| 4,741,736 A | | 5/1988 | Brown |
| 4,856,340 A | | 8/1989 | Garrison |
| 4,865,591 A | | 9/1989 | Sams |
| 4,883,472 A | | 11/1989 | Michel |
| 4,969,871 A | | 11/1990 | Theeuwes et al. |
| 4,973,318 A | | 11/1990 | Holm et al. |
| 5,017,190 A | | 5/1991 | Simon et al. |
| 5,026,357 A | | 6/1991 | Przuntek et al. |
| 5,250,023 A | * | 10/1993 | Lee et al. .................... 604/20 |
| 5,279,544 A | * | 1/1994 | Gross et al. ................. 604/20 |
| 5,279,586 A | | 1/1994 | Balkwill |
| 5,327,033 A | | 7/1994 | Guckel et al. |
| 5,330,431 A | | 7/1994 | Herskowitz |
| 5,354,279 A | | 10/1994 | Hofling |
| 5,391,250 A | | 2/1995 | Cheney, II et al. |
| 5,437,999 A | | 8/1995 | Diebold et al. |
| 5,457,041 A | * | 10/1995 | Ginaven et al. ............. 435/455 |
| 5,569,272 A | * | 10/1996 | Reed et al. .................. 606/151 |
| 5,587,326 A | | 12/1996 | Takemura |
| 5,637,095 A | | 6/1997 | Nason et al. |
| 5,640,995 A | | 6/1997 | Packard et al. |
| 5,644,177 A | | 7/1997 | Guckel et al. |
| 5,697,901 A | * | 12/1997 | Eriksson ...................... 604/46 |
| 5,716,343 A | | 2/1998 | Kriesel et al. |
| 5,914,507 A | | 6/1999 | Polla et al. |
| 5,964,729 A | | 10/1999 | Choi et al. |
| 5,997,501 A | | 12/1999 | Gross et al. |
| 6,016,693 A | | 1/2000 | Viani et al. |
| 6,022,316 A | | 2/2000 | Eppstein et al. |
| 6,050,988 A | * | 4/2000 | Zuck ......................... 604/20 X |
| 6,083,196 A | * | 7/2000 | Trautman et al. ............. 604/46 |
| 6,132,755 A | | 10/2000 | Eicher et al. |
| 6,256,533 B1 | | 7/2001 | Yuzhakov et al. |
| 6,334,856 B1 | | 1/2002 | Allen et al. |

* cited by examiner

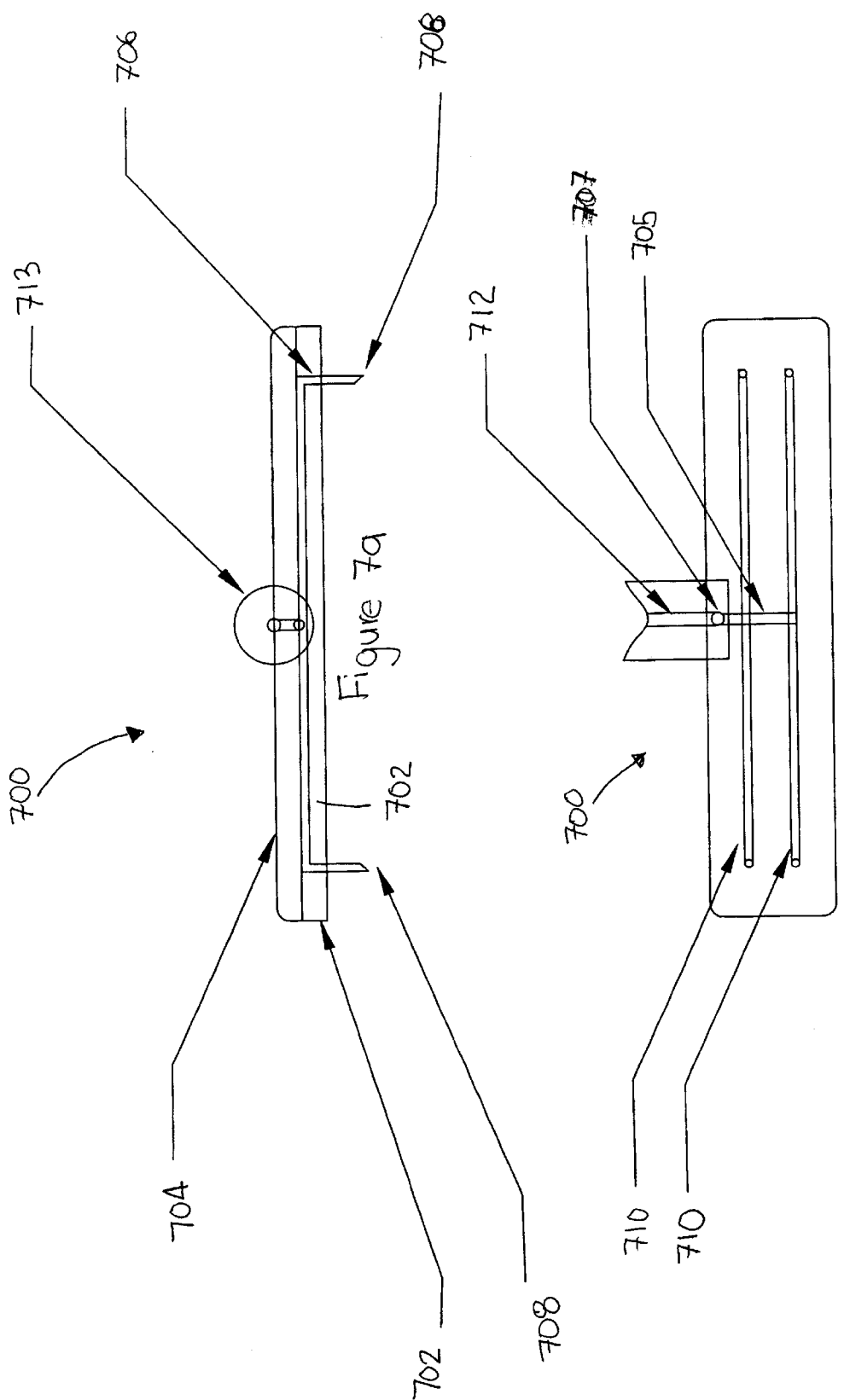

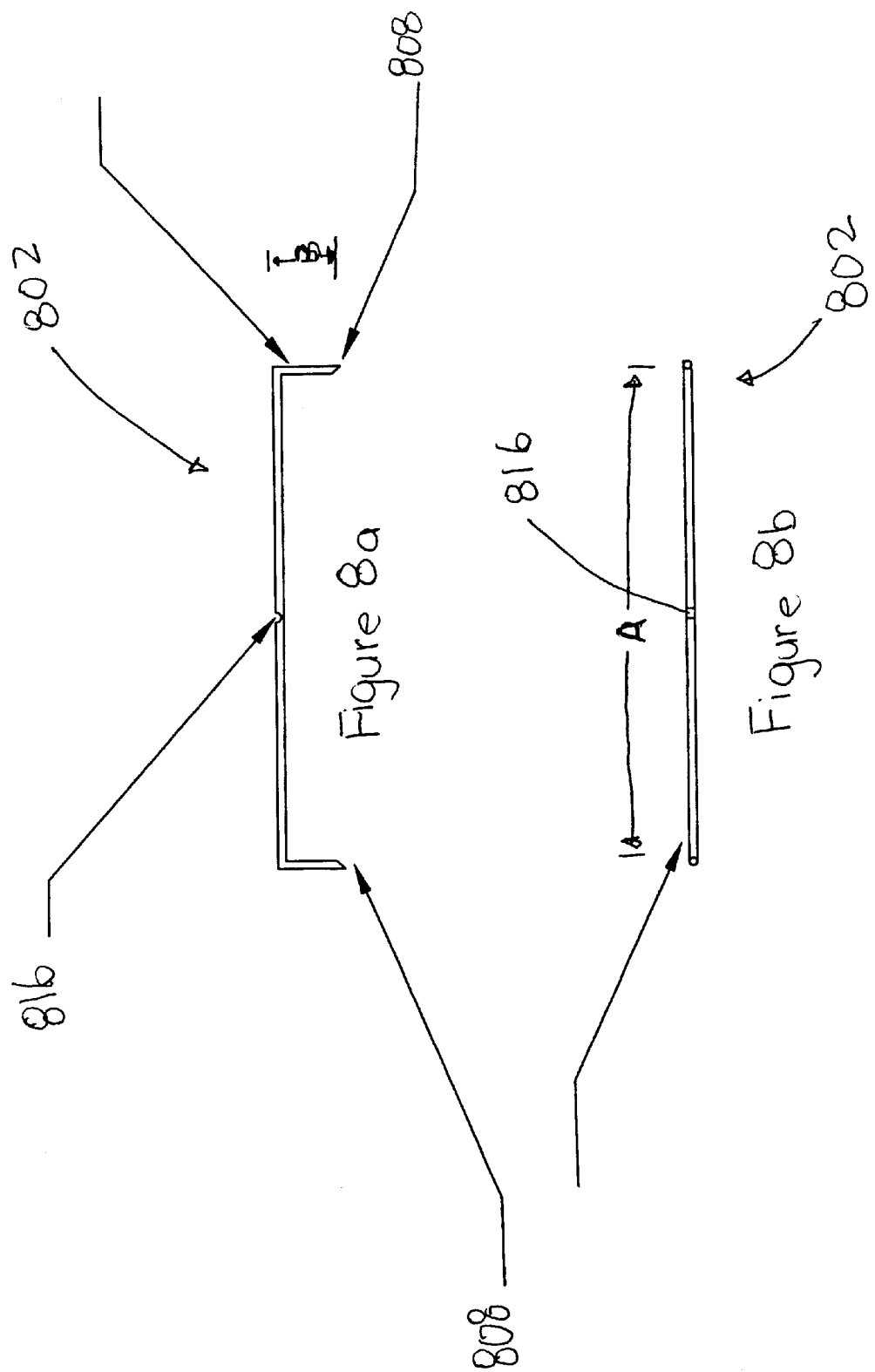

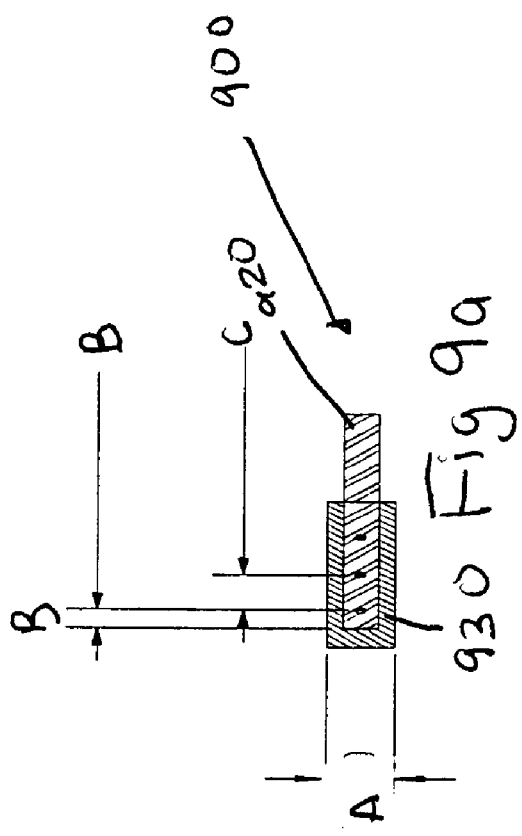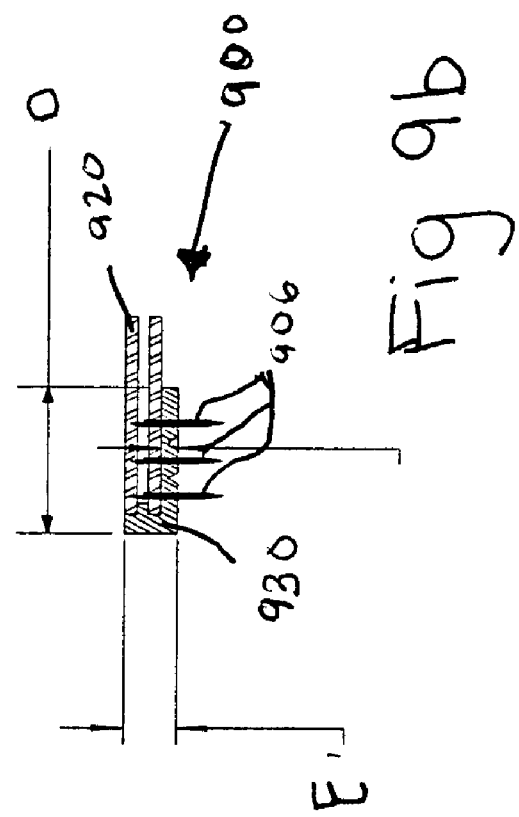

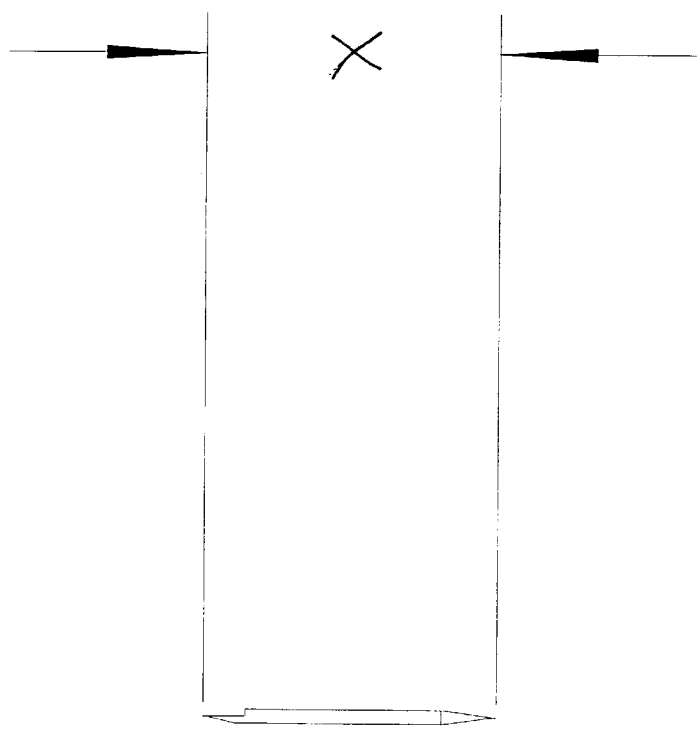

MICRO INFUSION DRUG DELIVERY DEVICE

The present application is related and claimed priority to U.S. application Ser. No. 60/202,818, filed May 8, 2000, by Joel Douglas, and U.S. application Ser. No. 60/223,630 filed Aug. 8, 2000, by Joel Douglas, the entire contents of each of which is incorporated by reference herein.

MICRO INFUSION DRUG DELIVERY DEVICE

1. Field of the Invention

The present invention relates to a medical device for administering a drug to a patient. More specifically, the present invention relates to a micro infusion drug delivery device.

2. Description of the Related Art

Infusion pumps are used to deliver various types of solutions subcutaneously to patients. There are many medical conditions that require the administration of liquid medicaments transcutaneously (through the skin) for prolonged periods. Diabetes, for example, may be controlled by daily, or more frequent, injections of insulin. The ability to administer numerous small dosages of insulin has been proven to be the best way to insure tight glucose control for a patient. The National Institute of Health (NIH) conducted a long-term study of people with diabetes known as the Diabetes Complications and Control Trial (DCCT) were it was determined that the proper management of diabetes requires 4 or more injections of insulin per day. However, current devices either are not convenient or easy to use by patients. Syringes and insulin pens all require the patients to inject themselves and do not provide a convenient or discreet mechanism to accomplish medication delivery.

Since transcutaneous injections are painful and troublesome, and since each injection represents a possibility for infection, injections are spaced at intervals as far apart as possible, resulting in peak and valley concentrations of the medicament in the bloodstream or at the site in the body requiring the medicament, the peak concentrations occurring shortly after the administration of the medicament and the low, or valley, concentrations occurring shortly before the administration of the next injection. This method of administration exposes the patient to the possibility of overdose at peak levels and underdose at valley levels, but was nevertheless the standard method for many years in the absence of a better alternative.

Recently, systems have been developed in which a catheter is semi-permanently implanted in a patient to provide access to a transcutaneous site in a patient's body, and a liquid medicament is supplied to the catheter from a reservoir. However, many patients find that the infusion site forms small red marks that are the result of irritation from the infusion at a single point. Infusing the medication either by bolus injection or reducing the amount of medication infused at any one specific site relieves this irritation.

U.S. Pat. No. 3,964,484 by Gerstel, et al. describes a drug delivery device for percutaneously administering a drug comprising a plurality of projections, a drug reservoir containing a drug, and where the projections extend from the reservoir and are adapted for penetrating the stratum corneum for percutaneously administering a drug from the reservoir to produce a local or systemic physiological or pharmacological effect.

U.S. Pat. No 4,235,234 discloses a subcutaneous injection system for injecting fluids in the subcutaneous fat layer of a patient including an injection needle having a sharpened end thereon for penetrating the subcutaneous fat layer of the patient and a locator pad carrying the needle with the locator pad having a locating surface to lie against the patient's skin from which the sharpened end of the needle projects a prescribed distance while oriented generally normal to the locating surface to positively control the depth of penetration of the sharpened end of the injection needle into the subcutaneous fat layer of the patient.

U.S. Pat. No. 4,969,871 discloses a drug formulation chamber for an intravenous administration set is provided. The intravenous administration set includes a container of an IV fluid, a drip chamber, a drug formulation chamber, and an adapter-needle assembly. The drug formulation chamber has a fluid inlet and a fluid outlet for maintaining a flow of IV fluid through the chamber. A portion of the chamber wall is comprised of a window material which allows the drug to diffuse therethrough but which prevents convective loss of the IV fluid. A flow distributor is provided within the chamber for distributing the flow of IV fluid along the interior surface of the window. A transdermal-type drug delivery device is adhered to the exterior surface of the window. Drug is delivered by the delivery device through the window and into the flowing IV fluid. The device delivers drug into the IV fluid at a rate that is independent of the flow rate of IV fluid through the formulation chamber. The rate of drug delivery from the device into the IV fluid is controlled by either the window itself or by a membrane layer in the drug delivery device. A plurality of drug delivery devices may be adhered to the window to deliver a plurality of drugs or to deliver a single drug at a higher dosage rate. A similar window may be placed in an IV bag to deliver a drug into the IV fluid therein.

U.S. Pat. No. 6,083,196 discloses a device comprising a sheet member having a plurality of microprotrusions for penetrating the skin and a substantially incompressible agent reservoir housing contacting and extending across the sheet member for transmitting a hold-down force applied the sheet member to maintain the microprotrusions in skin-piercing relation to the skin, even during and after normal patient body movement.

U.S. Pat. No. 6,050,988 discloses a device comprising a sheet member having a plurality of microprotrusions extending from a bottom edge for penetrating the skin of a patient. The sheet member when in use being oriented in an approximately perpendicular relation to the patient's skin.

U.S. Pat. No. 5,587,326 discloses a method and apparatus for mechanically disrupting a layer of skin having a known thickness without substantially disrupting underlying dermis layers below the layer of skin in question so as to facilitate the delivery of compounds across the disrupted layer. The apparatus includes a cutter having a plurality of microprotrusions having a height chosen with respect to the layer of skin that is to be disrupted and a stop for preventing the apparatus from penetrating the skin beyond a predetermined distance.

U.S. Pat. No. 6,022,316 discloses an apparatus and a method for electroporating tissue. At least one micropore is formed to a predetermined depth through a surface of the tissue, and electrical voltage is applied between an electrode electrically coupled to the micropore and another electrode spaced therefrom. By applying electroporation to tissue that has been breached by a micropore, the electroporation effects can be targeted at tissue structures beneath the surface, such as capillaries, to greatly enhance the withdrawal of biological fluid, and the delivery for uptake of compounds into the tissue.

SUMMARY OF THE INVENTION

It is a general object of the invention to provide a new and improved infusion pump which is adapted for use with pre-filled single dose containers and configured for use with a catheter or skin interface device configured from a plurality of micro projections either attached directly to the pump or by means of a catheter.

Another object of the invention is to provide a catheter which utilizes a skin interface device that breaches the stratum corneum with multiple lumin projections and is connected to a micro infusion device that is capable of providing a relatively constant infusion of medication or bolus injections on demand. This gives the patient a more comfortable infusion and minimizes the irritation from the infusion process.

Another object of the invention is the formation of the micro projection lumens from micro-machined components using semi conductor processes.

Another object is to provide an infusion pump of the type described which eliminates the need for the patients to separately transfer the medications into containers used with the pump, and thereby minimize costly preparation steps.

Another object is provide an infusion pump of the type described which accurately dispenses the medication at a controlled pressure and for a controlled period of time which enables the use of a micro projection skin interface device.

Another object is to provide an infusion pump of the type described which includes a control system with safety features.

Another object is to provide an infusion pump of the type described which achieves health benefits by obviating the risk of contaminating the medication by transferring the medication from primary container to one which is compatible with the pump and providing an alarm in the case where the solution is not completely delivered to the patient.

Another object is to provide an infusion pump which is small in size to permit discrete infusion of medication.

Another object is to provide an infusion pump of the type described which accurately dispenses medication at a controlled pressure and for a controlled period of time.

Another object is to provide an infusion pump of the type described which includes a control system with is capable of supporting both basal rate delivery and bolus delivery.

Another object is to provide an infusion pump of the type described which achieves health benefits by obviating the risk of contaminating medication solution by using prefilled cartridges The foregoing and additional objects and features of the invention will appear from the following specification in which the several embodiments have been set forth in detail in conjunction with the accompanying drawings.

BRIEF DESCRIPTION IF THE DRAWINGS

A brief description of the drawings are as follows:

FIG. 7a illustrates a side sectional view of the holder and needle in a closed position;

FIG. 7b illustrates a bottom view of the holder and needle in a closed position;

FIG. 8a illustrates a side view of the needle;

FIG. 8b illustrates a top view of the needle;

FIGS. 9a and 9b illustrate another exemplary embodiment of the micromachined projections of the skin interface device; and FIG. 10 illustrates a side view of one needle.

DETAILED DESCRIPTION IF THE INVENTION

Figure 1:
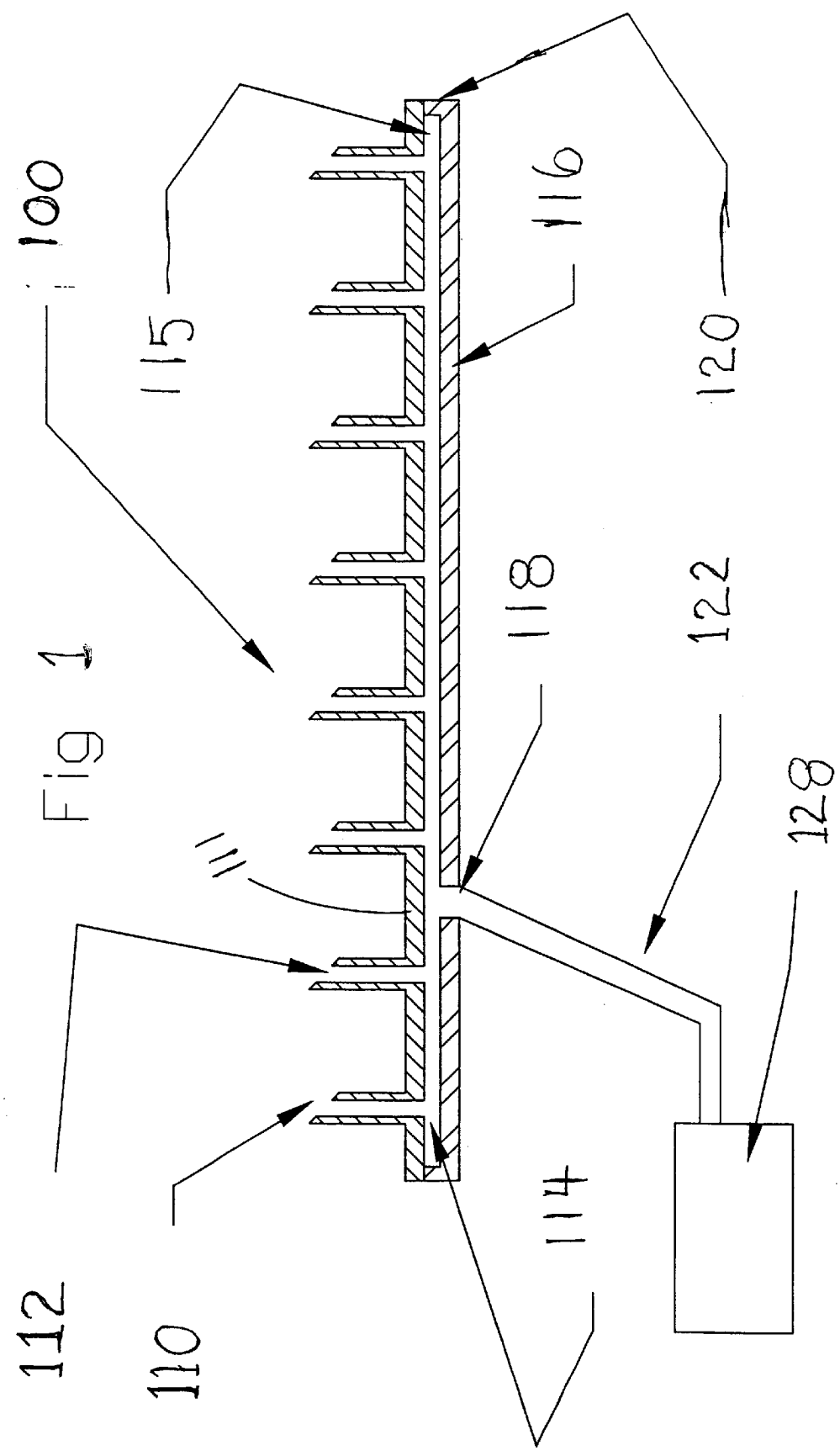
FIG. 1 illustrates a side sectional view of the micro machined projections of the skin interface device.

FIG. 1 is an elevation view of a micro-machined projections of the skin interface device 100. The exemplary embodiment shown in FIG. 1 includes a plurality of micro machined projections 110 which are able to puncture a patient's skin. The projections are formed from semiconductor materials and they are made by applying photo resist and etching the configurations into the wafer. These types of material allow for the skin interface device 100 and its respective components to have a higher tolerance level allowing for many advantages. The projections can be made any length by adding material to the projections by plating gas discharge or sputtering operations and reapplying a photo resist to etch the geometeries into the layers. Also, it should be appreciated that applicant use the term "plenum" to refer to passageways formed with the skin interface device 100.

In an exemplary embodiment of the present invention, the microprotrusions include blades that generate cuts in the layer of skin. The cuts are generated by moving the apparatus parallel to the surface of the skin either at the time of application, during the normal movements of the individual wearing the apparatus, or both. Additionally, the appropriate length of blade is determined for each individual and delivery site on that individual.

A holder 111 is comprised of a plurality of micro machined projections 110 which are built up from a series of etching and deposition steps that form the cannua shape micro projections 110 with the fluid delivery hole 112. The plenum 114 is formed by attaching an etched part 116 that has an open portion 115 and attaching it to the cannula holder 111 with an attachment means 120. Such attachment means include clamps, screws, heating, adhesive or other known methods to one skilled in the art. In the exemplary embodiment in FIG. 1 the attachment means 120 is an adhesive.

The feed port 118 is then attached to the catheter connecting tube 122 or directly to the pump 128. The materials which can be used to fabricate the skin interface device 100 are silicon oxide, gold, silver, carbon, or any other material which is capable to be deposited or machined with semiconductor or chemical methods. It should be appreciated that the pump can be a medication delivery device as described in Attorney Docket Number 032994-012, "Reusable Medication Delivery Device", Joel Douglas et al., filed on Sep. 29, 2000.

Figure 2:
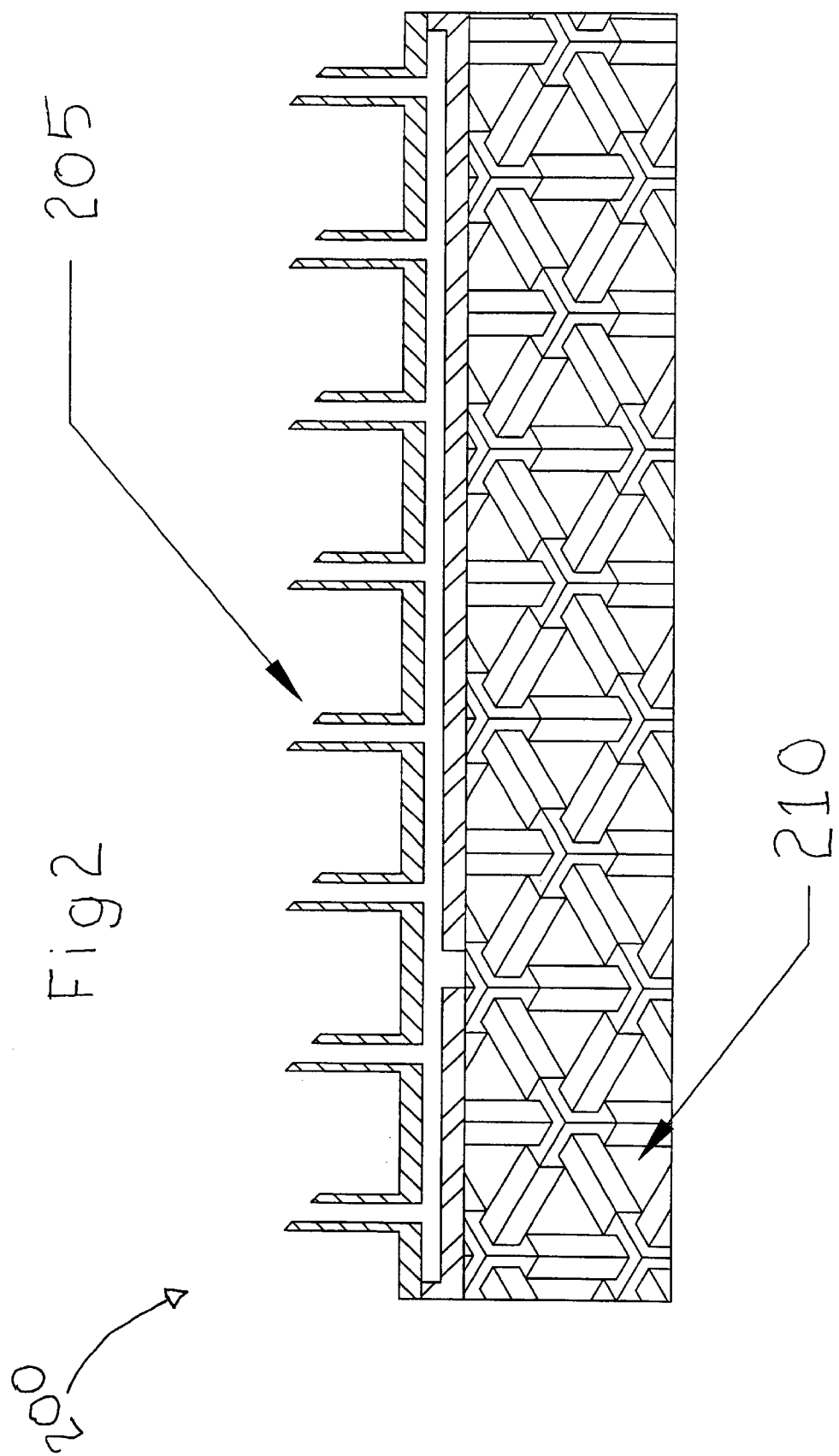
FIG. 2 illustrates a side sectional view of the micro machined projections of the skin interface device in direct contact with a pump.

FIG. 2 illustrates an exemplary embodiment wherein the skin interface device 200 has the micro machined projections 205 mounted in direct communication with the pump 210.

Figure 3:
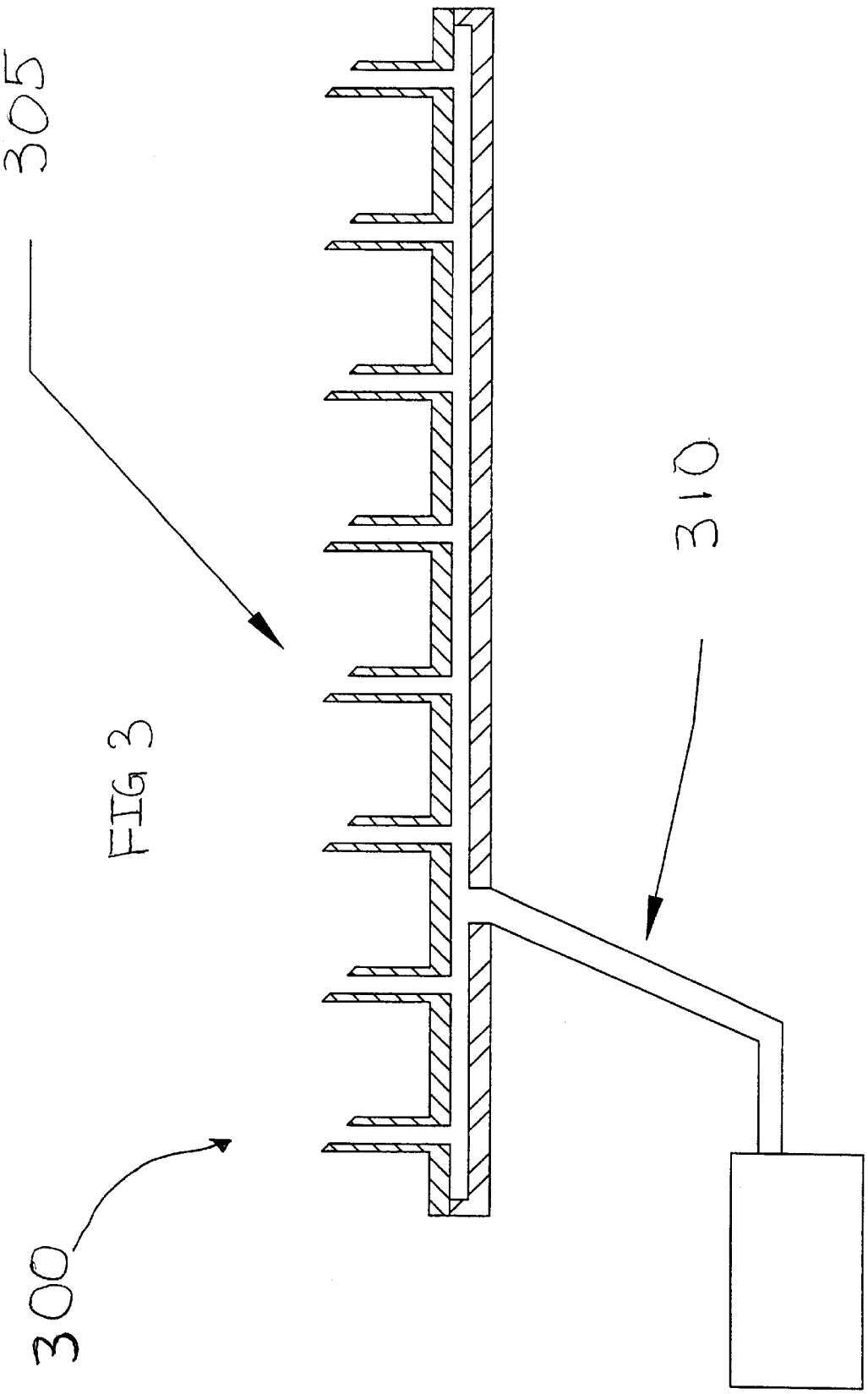
FIG. 3 illustrates a side sectional view of the micro machined projections of the skin interface device in contact with a catherer.

FIG. 3 illustrates an exemplary embodiment wherein the skin interface device 300 includes a catheter configuration 310 which is connected to the skin interface device 305 of the present invention.

Figure 4:
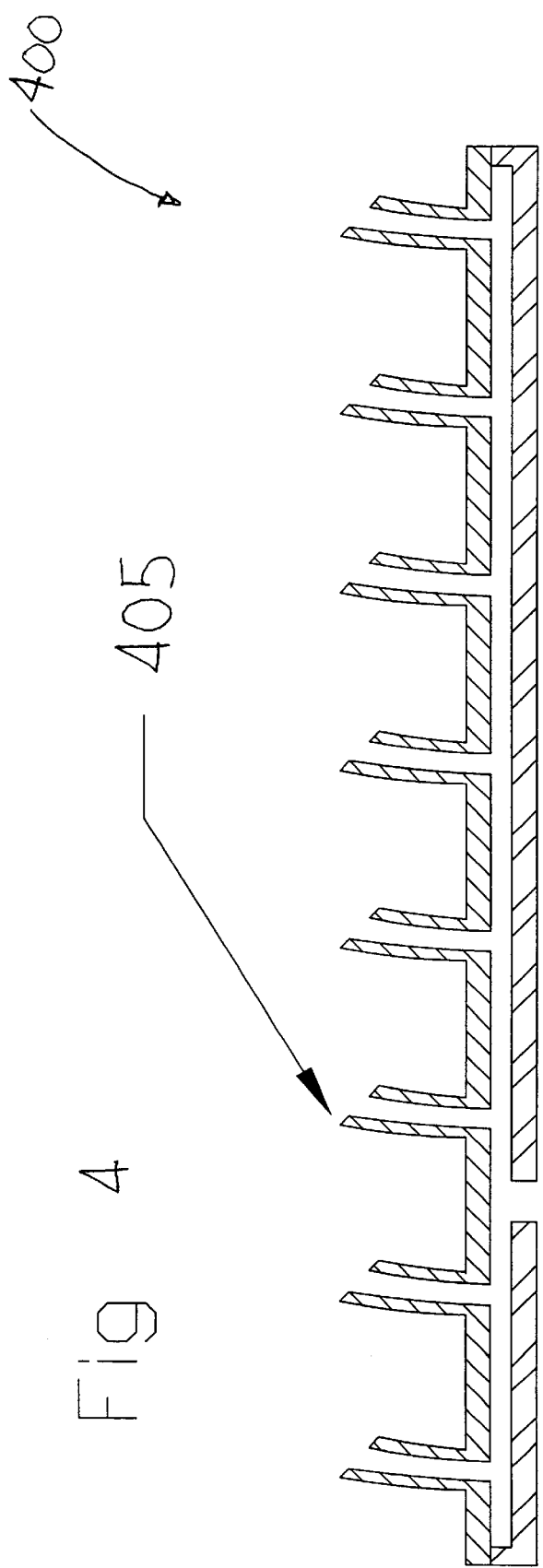
FIG. 4 illustrates a side sectional view of the micro machined projections of the skin interface device with curved projections.
Figure 5:
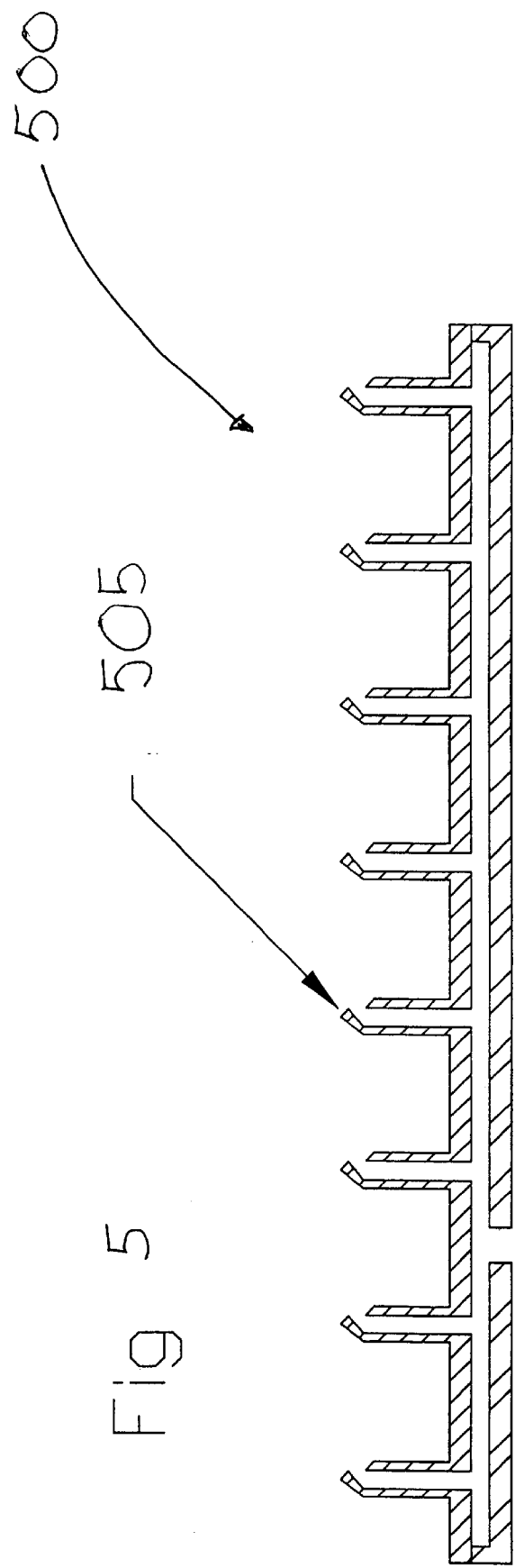
FIG. 5 illustrates a side sectional view of the micro machined projections of the skin interface device with bent projections.

FIG. 4 illustrates an exemplary embodiment wherein the skin interface device 400 includes a plurality of projections 405 which have a slightly curved shape. The small micro projections 405 can be formed such that they have a slight curve in the direction of penetration. This has the added benefit by reducing the amount of irritation from the infusion because a small pocket in the skin is formed by the curve in the cannula as shown in FIGS. 4 and 5. The same beneficial affect is found when using traditional needles and forming either a curve in them or as shown in FIG. 5 adjusting the projections 505 so it forms an angle with the shaft between 1 and 35 degrees where as in the preferred embodiment the angle is about 10 degrees.

Because many patients find that the infusion site forms small red marks that are the result of irritation from the infusion at a single point. Infusing the medication either by bolus injection or reducing the amount of medication infused at any one specific site relieves this irritation. The present invention provides a catheter or injection device that is formed from numerous micro projections that result in three improvements, amongst other improvements, over the related art. The first is the reduction and elimination in certain patients of irritation marks from the infusion of medication to one site. The second is the reduction in the bulk of the infusion hub at the patient's skin. This results in a more convenient and discrete package for the patient. The third benefit is the reduction in pain felt by the patient when inserting the infusion device.

Figure 6A:
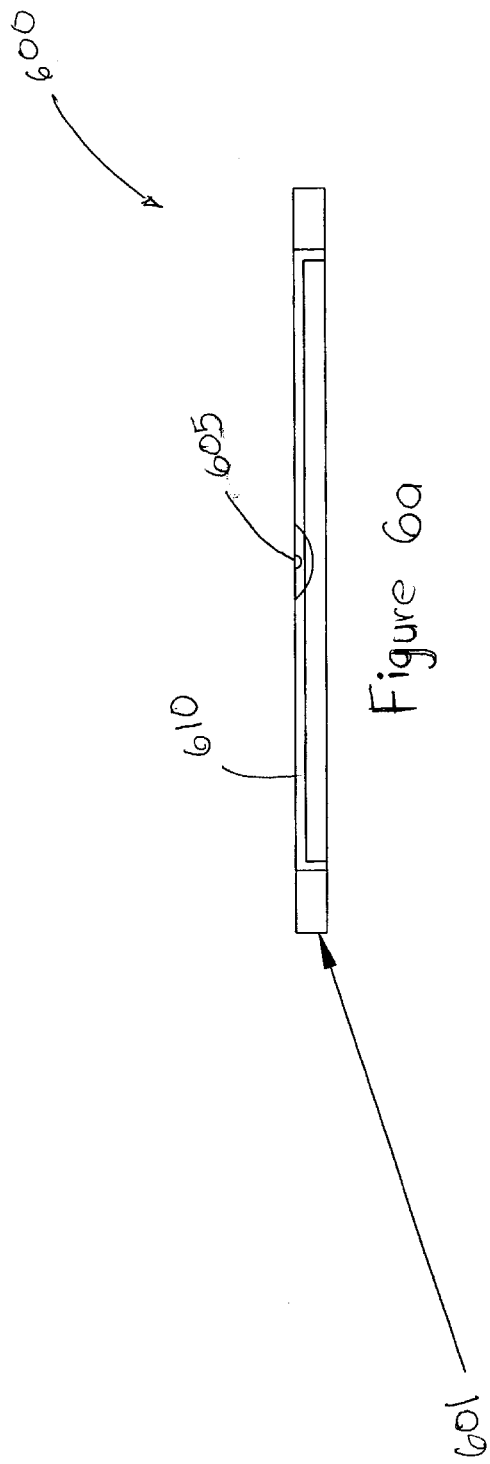
FIG. 6a illustrates a side section view of the bottom portion of a holder.
Figure 6B:
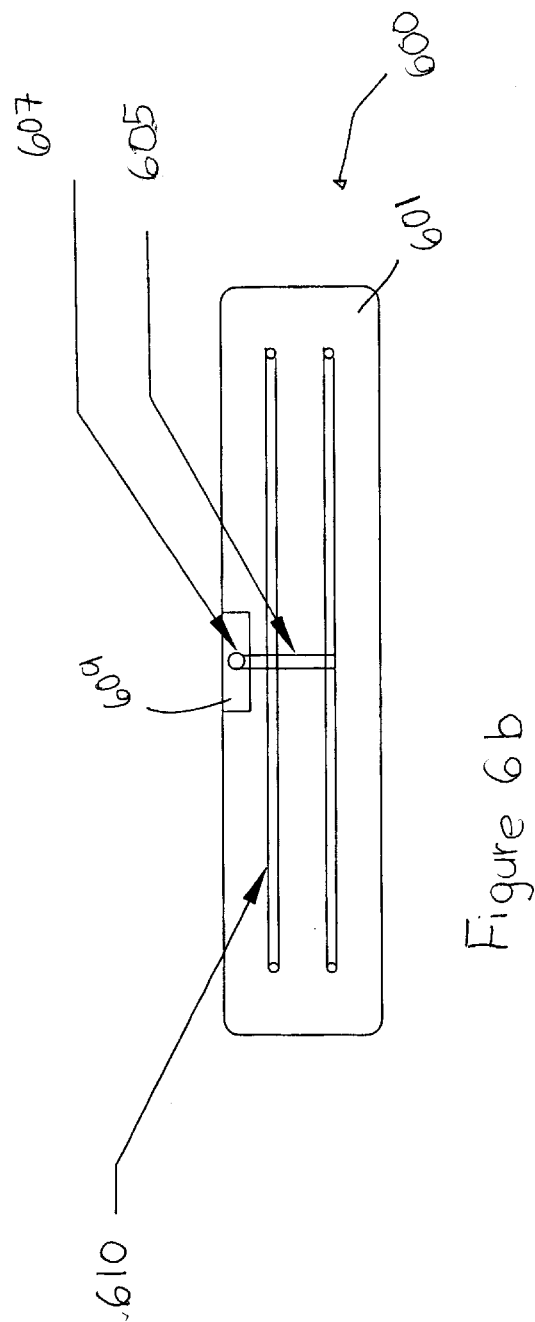
FIG. 6b illustrates a bottom view of the bottom portion of a holder.

FIGS. 6a and 6b illustrates an exemplary embodiment of the present invention of a bottom portion of a holder 600, wherein FIG. 6a is a side section view of the holder 600 and FIG. 6b is a bottom view of the holder 600. As shown in the figures, the holder 600 has at least one groove 610 running across the body of the holder 600. The holder may be formed from either injection molded plastic or from etching a base material including, but not limited to, silicon, aluminum, glass or the any like material known to one skilled in the art. Furthermore, the holder 600 includes a first plenum feed 605 and a second plenum feed 607 formed within the holder 600. In the exemplary embodiment the first plenum runs along the top plane of the body of the holder 600, whereas the second plenum 607 runs at an angle to the body of the holder 600. In the preferred embodiment the second plenum 607 runs in a substantially perpendicular angle to the body of the holder 600 and is received by the first plenum 605. The holder 600 also includes an receded portion 609.

FIGS. 7a and 7b illustrate the holder 700 in connection with the needle 702 in a closed position. The holder 700 is comprised of a bottom portion 702 and a top portion 704. A needle 706 is able to be received between the bottom portion 702 and the top portion 704 as shown in FIG. 7a. In the exemplary embodiment shown in FIGS. 7a and 7b the needle 706 comprises at least one double ended needle 706 which has needle points 708 located near each end of the needle 706. However, the needle points 708 may be located anywhere along the needle 706. In the exemplary embodiment the needle 706 has a general U-shaped configuration as shown in the figure, however, other shapes may be configured depending on the placement of the needle, patient's body shape, desired use of the needle and any other requirements as needed by the user.

As shown in FIGS. 7a and 7b the first plenum 705 is located on both the bottom portion 702 and the top portion 704 of the holder 700 and runs in a substantially perpendicular direction to the grooves 710 located on the bottom portion 702. The first plenum is connected to the grooves 710 which are located on the bottom portion 702 and is also connected to the second plenum 707. In the exemplary embodiment shown in FIGS. 7a and 7b, the second plenum 707 is substantially perpendicular to the first plenum 705. Therefore, the first plenum 705, the second plenum 707 and the passageway 712 form a passageway which allows various types of fluid to flow into and out of the device as necessary.

As shown in FIGS. 8a and 8b is a side view and a top view of the exemplary needle 802, respectively. A groove 816 is made in the needle 802 so that the groove 816 will align with the first plenum 705 located in the top portion 704. In the preferred embodiment, the needle 802 is approximately 1.00 inches long A and the protruding portions B are approximately 0.125 inches in length and the needle has a thickness of approximately 0.1 inches.

FIGS. 9a and 9b illustrate another exemplary embodiment of the present invention. FIG. 9a is a top view of the exemplary embodiment illustrating a skin interface device 900 comprising a tube 920 and a base 930 which attachably receives the tube. Furthermore, the tube 920 and the base 930 contain openings which align with each other when all the members are properly configured as shown in FIGS. 9a and 9b. These openings are able to receive the needle 906. A detailed view of the needle 906 can be seen in FIG. 10.

It should be appreciated that the tube is made from LDPE material and the base is made from plastic. In the exemplary embodiment there are three needles 906 that are 30 gauge needles with a length of about 0.1 inches to 0.2 inches, but preferably 0.134 inches (as shown in FIG. 10 reference (X)).

In the exemplary embodiment, the dimensioning for the skin interface device is as follows; A is in the range of about 0.05 inches to 0.15 inches; C is the distance between the needles in the range of about 0.050 to 0.15 inches; B is the range of about 0.025 to 0.075; D is in the range of about 0.020 to 0.060 inches; E is in the range of about 0.03 to 0.12 inches. However the dimensions may change depending on the user's desire as needed.

While the invention has been described in detail with reference to preferred embodiments thereof, it will be apparent to one skilled in the art that various changes can be made, and equivalents employed, without departing from the scope of the invention. Each of the foregoing references and documents are incorporated by reference herein in each of their entireties.

What is claimed is:

1. A skin interface device, comprising:

a bottom portion;

a top portion which is attached to the bottom portion;

a plurality of projections located on the top portion, each of the plurality of projections has an opening extending therethrough, and wherein the projections extend in a direction non-perpendicular to the top portion;

a first passageway formed between the bottom portion and the top portion;

a second passageway formed on the bottom portion wherein the first passageway, the openings extending through the projections and the second passageway are interconnected so that fluid is able to flow through the second passageway into the first passageway and then into each respective opening extending through each of the plurality of projections and wherein at least a portion of the openings extending through the projections are non-perpendicular to the top portion.

2. The skin interface as claimed in claim 1, wherein the top portion and the bottom portion are attached by an adhesive.

3. The skin interface as claimed in claim 1, wherein the projections are made by plating gas discharge or sputtering operations and reapplying a photo resist to etch the geometries into layers.

4. The skin interface as claimed in claim 1, wherein a pump is connected to the skin interface through the second passageway.

5. The skin interface as claimed in claim 1, wherein the projections are curved.

6. A skin interface device, comprising:

a bottom portion;

a top portion which is attached to the bottom portion;

a plurality of projections located on the top portion, each of the plurality of projections has an opening extending therethrough;

a first passageway formed between the bottom portion and the top portion;

a second passageway formed on the bottom portion wherein the first passageway, the openings extending through the projections and the second passageway are interconnected so that fluid is able to flow through the second passageway into the first passageway and then into each respective opening extending through each of the plurality of projections and wherein at least a portion of the openings extending through the projections are non-perpendicular to the top portion, wherein the projections are bent at an angle.

7. A skin interface device, comprising:

a bottom portion;

a top portion which is attached to the bottom portion;

a plurality of projections located on the top portion, each of the plurality of projections has an opening extending therethrough;

a first passageway formed between the bottom portion and the top portion;

a second passageway formed on the bottom portion wherein the first passageway, the openings extending through the projections and the second passageway are interconnected so that fluid is able to flow through the second passageway into the first passageway and then into each respective opening extending through each of the plurality of projections and wherein at least a portion of the openings extending through the projections are non-perpendicular to the top portion, wherein at least a portion of the openings extending through the projections are disposed at an angle of less than 35 degrees to an axis perpendicular to the top portion.

8. A skin interface device, comprising:

a bottom portion;

a top portion which is attached to the bottom portion;

a plurality of projections located on the top portion, each of the plurality of projections has an opening extending therethrough;

a first passageway formed between the bottom portion and the top portion;

a second passageway formed on the bottom portion wherein the first passageway, the openings extending through the projections and the second passageway are interconnected so that fluid is able to flow through the second passageway into the first passageway and then into each respective opening extending through each of the plurality of projections and wherein at least a portion of the openings extending through the projections are non-perpendicular to the top portion, wherein at least a portion of the openings extending through the projections are disposed at an angle of about 10 degrees to an axis perpendicular to the top portion.

* * * * *